United States Patent [19]

Suzuki et al.

[11] 4,051,318

[45] * Sept. 27, 1977

[54] PROCESS FOR PREPARING FORMATE ESTERS OF ALKYL-SUBSTITUTED AROMATIC HYDROXY COMPOUNDS

[75] Inventors: Takashi Suzuki; Susumu Naito, both of Niigata, Japan

[73] Assignee: Mitsubishi Gas Chemical Company, Inc., Tokyo, Japan

[*] Notice: The portion of the term of this patent subsequent to Aug. 24, 1993, has been disclaimed.

[21] Appl. No.: 646,594

[22] Filed: Jan. 5, 1976

[30] Foreign Application Priority Data

Jan. 16, 1975 Japan .................................. 50-7210
Apr. 18, 1975 Japan .................................. 50-47260

[51] Int. Cl.² ............................................... C07C 69/06
[52] U.S. Cl. .................................................. 560/131

[58] Field of Search ..................... 260/479 R

[56] References Cited

U.S. PATENT DOCUMENTS 3,976,702  8/1976  Suzuki et al. ................... 260/621 R

FOREIGN PATENT DOCUMENTS 25,043  3/1974  Japan .................................. 260/479

Primary Examiner—Jane S. Myers
Attorney, Agent, or Firm—Wenderoth, Lind & Ponack

[57] ABSTRACT

Formate esters of the general formula HCOOAr wherein Ar is an aromatic hydrocarbon group containing an alkyl substituent are prepared by oxidizing alkyl aromatic aldehydes of the general formula ArCHO wherein Ar is the same as defined above with organic peroxy acids in the presence of hydrogen fluoride.

13 Claims, 1 Drawing Figure

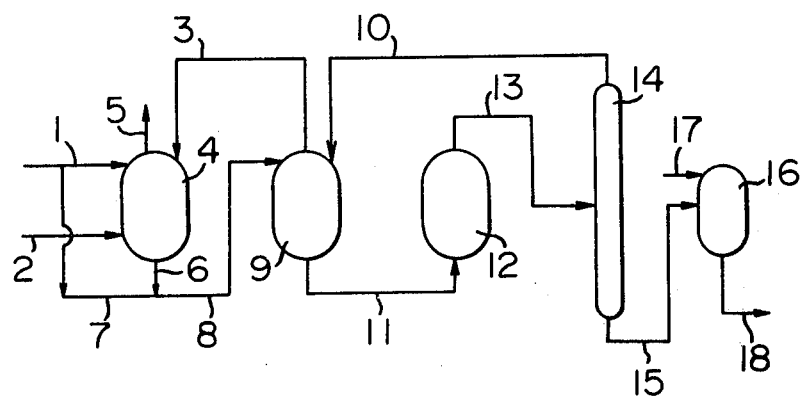

PROCESS FOR PREPARING FORMATE ESTERS OF ALKYL-SUBSTITUTED AROMATIC HYDROXY COMPOUNDS

This invention relates to a process for preparing formate esters of alkyl-substituted aromatic hydroxy compounds by oxidizing corresponding alkyl aromatic aldehydes.

The formate esters of alkyl-substituted aromatic hydroxy compounds, such as alkyl phenols, can be raw materials for the corresponding alkyl-substituted aromatic hydroxy compounds. The alkyl-substituted aromatic hydroxy compounds can be prepared easily and quantitatively by hydrolysis or ester-interchange of the formate esters of alkyl-substituted aromatic hydroxy compounds by means known per se. The alkyl-substituted aromatic hydroxy compounds are industrially important materials that are useful, for example, for the production of synthetic resins, plasticizers, antioxidants and agricultural chemicals.

It has been known that alkylphenols are prepared by separation from tar acids. Since the tar acids contain a number of alkylphenol isomers and homologs with small differences in properties among them, it is extremely difficult to separate out the individual components in pure form. Accordingly, the speuration from tar acids is disadvantageous as a commercial process for preparing high purity alkylphenols. Synthesizing methods have also been developed, but have not proved satisfactory. For example, a method comprising melting alkylphenylsulfonic acid salts with alkalies yields isomers as by-products and a great quantity of waste matter. Methods similar to the cumene process, such as the production of cresol by the cymeme process, on the other hand, have the defect that the cost of installation is high, and large quantities of by-products are formed.

The present invention provides a process for preparing formate esters of alkyl-substituted aromatic hydroxy compounds by oxidizing alkyl aromatic aldehydes, and an advantageous process for preparing the alkylsubstituted aromatic hydroxy compounds which may be derived from the formate.

The oxidation of alkyl aromatic aldehydes to formate esters of alkyl-substituted aromatic hydroxy compounds is known as a king of the Baeyer-Villiger reaction, and generally, organic peroxy acids are used as oxidizing agents. However, the Baeyer-Villiger reaction using organic peroxy acids as oxidizing agents has a low rate of reaction, and this defect is scarcely improved even in the presence of ordinary acid catalysts (Japanese Laid-Open patent application Nos. 27933/72, 27934/72, and 56635/73). Moreover, since aromatic aldehydes generally tend to be oxidized to aromatic carboxylic acids, the rate of reaction and selectivity in the synthesis of formate esters of the alkyl-substituted aromatic hydroxy compounds by the Baeyer-Villiger reaction are not satisfactory.

We made extensive investigations in order to remove these defects of the prior art techniques, and already developed a process for selectively preparing formate esters of alkylphenols by oxidizing alkyl aromatic aldehydes with hydrogen peroxide in the presence of hydrogen fluoride (Japanese patent application No. 25043/74). According to this process, water is formed from the hydrogen peroxide, and since water and hydrogen fluoride form an azeotropic mixture, it is substantially impossible to separate and recover hydrogen fluoride. Furthermore, since water reduces the catalytic action of hydrogen fluoride, the azeotropic mixture of hydrogen fluoride and water, even when recovered, cannot be directly used again in the oxidation reaction.

We have furthered our investigations with a view to getting over this difficulty, and finally arrived at this invention. The present invention is based on the discovery that when alkyl aromatic aldehydes are oxidized with organic peroxy acids in the presence of hydrogen fluoride, formate esters of the corresponding alkyl-substituted aromatic hydroxy compounds can be easily and selectively prepared.

It is therefore an object of this invention to provide a process for preparing formate esters of alkylsubstituted aromatic hydroxy compounds which remove the various defects of the prior art techniques and give satisfactory rates of reaction and selectivity, and in which the hydrogen fluoride can be easily recovered without reducing the catalytic action.

According to this invention, there is provided a process for preparing formate esters of the general formula HCOOAr 

wherein Ar is an aromatic hydrocarbon group containing an alkyl substituent, which comprises oxidizing an alkyl aromatic aldehyde of the general formula ArCHO 

wherein Ar is the same as defined above, with an organic peroxy acid in the presence of hydrogen fluoride in the presence or absence of a solvent.

The alkyl aromatic aldehydes are oxidized to the formate esters of the corresponding alkyl-substituted aromatic hydroxy compounds by the process of this invention while maintaining the relative positions of the alkyl substituents. Accordingly, when alkyl aromatic aldehydes having high purity are used, high purity formate esters of alkylsubstituted aromatic hydroxy compounds, and hence high purity alkyl-substituted aromatic hydroxy compounds can be obtained.

The alkyl aromatic aldehydes used in this invention are mononuclear, polynuclear and of fused fing type, and the nomonuclear aldehydes are especially preferred. The number of the alky groups in the mononuclear alkyl aromatic aldehydes is 1 to 5. The alkyl groups of the alkyl aromatic aldehydes are preferably lower alkyl groups. Examples of especially preferred alkyl aromatic aldehydes are o-tolualdehydes, m-tolualdehyde, p-tolualdehyde, 2,4-dimethylbenzaldehyde, 2,5-dimethylbenzaldehyde, 3,5-dimethylbenzaldehyde, 2,4,5-trimethylbenzaldehyde, and 4-isopropylbenzaldehyde. These alkyl aromatic aldehydes can be used either alone or as mixtures of two or more. Furthermore, these alkyl aromatic aldehydes can be used as solutions in saturated hydrocarbons or aromatic hydrocarbons.

Examples of the organic peroxy acids used in this invention are o-peroxytoluic acid, m-peroxytoluic acid, p-peroxytoluic acid, peroxybenzoic acid, peroxyacetic acid, peroxyformic acid, peroxypropionic acid, peroxyisobutyric acid, trifluoroperoxyacetic acid, and monoperoxyphthalic acid. The p-peroxytoluic acid, peroxybenzoic acid and peroxyacetic acid are relatively easily available in anhydrous form, and are therefore prefered. The p-peroxytoluic acid can be readily obtained in anhydrous form by the autoxidation of p- tolualdehyde, and because of its freedom from the danger of explosion, is especially preferred. The autoxidation of p-tolualdehyde can be carried out in a customary manner by oxidizing it with oxygen or air in a suitable solvent such as acetone in the absence of catalyst or in the presence of a heavy metal salt catalyst.

The hydrogen fluoride used as a catalyst in the process of this invention is preferably anhydrous.

The process of this invention can be carried out in the absence of a solvent, but generally, the use of solvents is preferred. When no solvent is used, it sometimes happens that the reaction mixture becomes tarry and the intended final product can scarcely be obtained. The solvent used in this invention is a oxygen-containing compound such as a lower aliphatic carboxylic acid, ester, ether or ketone. Of these, acetic acid, ethyl acetate and acetone etc. are especially preferred. The use of the solvents makes it possible to dissolve the crystalline alkyl aromatic aldehyde or crystalline organic peroxy acid and to perform the reaction smoothly. It is also effective for inhibiting side reeactions.

When tolualdehyde is oxidized with peroxytoluic acid in the presence of hydrogen fluoride, acetone is especially preferred as the solvent since the formate ester of cresol can be prepared smoothly and selectively, and the hydrogen fluorice and acetone can be recovered as an azetropic mixture.

The presence of water in the reaction system causes a decrease in the amount of hydrogen fluoride to be recovered in an anhydrous form. When the hydrogen fluoride is to be recovered and re-used, therefore, it is preferred to use the alkyl aromatic aldehyde, organic peroxy acid, hydrogen fluoride and solvent each having a low content of water. Even when these materials contain water, they can be used in the process of this invention.

The amount of the organic peroxy acid is not particularly restricted. But in order to increase the conversion of the alkyl aromatic aldehyde, it is preferred to adjust the molar ratio of the organic peroxy acid to the alkyl aromatic aldehyde to at least 1.0, especially 1.0 to 1.3. No particular advantage can, however, be obtained even if the molar ratio is made larger than 1.5.

The amount of hydrogen fluoride is 0.5 to 4.0, preferably 0.8 to 1.2, in terms of its molar ratio to the total moles of the oxygen-containing compounds used (the alkyl aromatic aldehyde, organic peroxy acid, solvent, etc.). When the molar ratio is less than 0.5 the catalytic action of hydrogen fluoride is weak, and feasible rates of reaction cannot be obtained. When it is larger than 4.0, many side reactions occur, and the selectivity is low. When the reaction is carried out in the solvent, the amount of the solvent is determined so that the molar ratio of the hydrogen fluoride to the alkyl aromatic aldehyde is 3 to 20, preferably 5 to 15, and the amount of the hydrogen fluoride also meets the above-described requirement.

The reaction temperature is not critical in particular. But in order to perform the reaction smoothly, it is preferably −50° C. to + 50° C., more preferably −20° C. to + 20° C. The reaction pressure is essentially irrelevant to the reaction in accordance with this invention, but generally, the pressure is such as to maintain the reaction mixture in the liquid phase. The reaction can also be carried out at reduced pressure.

Under the above conditions, the alkyl aromatic aldehyde in nearly all its amount can be converted within 1 hour. For example, at a reaction temperature of 0° 1 C., almost all the alkyl aromatic aldehyde can be converted in 10 to 35 minutes.

The process of this invention can be carried out either batchwise or continuously. When the process is carried out batchwise, the addition of hydrogen fluoride to a mixture of the alkyl aromatic aldehyde and the organic peroxy acid induces reaction abruptly, and is very dangerous. It is preferred therefore to feed the materials in other sequences. For example, good results can be obtained by adding the organic peroxy acid to a mixture of the alkyl aromatic aldehyde and hydrogen fluoride, or a mixture of the hydrogen fluoride and organic peroxy acid to the alkyl aromatic aldehyde.

The catalytic action of hydrogen fluoride renders the organic peroxy acid highly active, and makes it possible to complete the reaction at low temperatures within short periods of time. Accordingly, side reactions are very much suppressed, and the selectivity of each of the alkyl aromatic aldehyde and organic peroxy acid to the formate ester of an alkyl-substituted aromatic hydroxy compound is high. Although it is known that the Baeyer-Villiger reaction as in the present invention is promoted by a strongly acidic catalyst, it is surprising that hydrogen fluoride which is generally belongs to weak acids (the pKa of hydrogen fluoride at 25° C. is 3.173) shows a superior catalytic action. In the process of this invention, water is not formed as a result of the reaction, and hydrogen fluoride recovered from the reaction mixture either singly or together with the solvent has a very high catalytic activity. Hence, it can be recycled as such without treating it in particular. By the hydrolysis or ester interchange of the resulting formate ester of alkyl-substituted aromatic hydroxy compound, the corresponding alkyl-substituted aromatic hydroxy compound can be prepared.

Preparation of a formate ester of cresol by oxidation of tolualdehyde with peroxytoluic acid in acetone in the presence of hydrogen fluoride in the substantially anhydrous state is one prefered embodiment of this invention. This embodiment will be described below with regard to an example of preparing a formate estero of p-cresol by oxidizing p-tolualdehyde with p-peroxytoluic acid.

The p-tolualdehyde used in this embodiment is one prepared by any desired method. For example, it is obtained by autoxidation of p-xylene, oxidation of p-xylene with an oxidizing agent, or reaction of toluene with carbon monoxide. In order to prepare high purity formate ester of p-cresol, and hence high purity p-cresol, it is preferred to use high purity p-tolualdehyde. In this regard, p-tolualdehyde prepared from toluene and carbon monoxide is preferred because it can be purified by a simple method.

In this embodiment, substantially anhydrous p-peroxytoluic acid is used. For example, p-peroxytoluic acid prepared by the autoxidation of p-tolualdehyde is conveniently used in this embodiment because it is substantially anhydrous. The autoxidation of p-tolualdehyde for preparing p-peroxytoluic acid is carried out by a conventional process which comprises oxidation with oxygen or air in s suitable solvent in the absence of catalyst or in the presence of a heavy metal salt catalyst. Acetone is superior as a solvent for autoxidation. When acetone is used as a solvent for autoxidation, crystals of p-peroxytoluic acid are separated by removing acetone from the autoxidation product and used as such, or the autoxidation product itself as a acetone solution of p-peroxytoluic a cid can also be used. Furthermore, the autoxidation is stopped halfways to conert a part of the p-tolualdehyde to p-peroxytoluic acid, and the resulting reaction mixture as an acetone solution of p-tolualdehyde and p-peroxytoluic acid can be used.

In this embodiment, substantially anhydrous acetone is used. Usually, acetone of commercial grade, dehydrated and purified in a customary manner, is conveniently used.

The hydrogen fluoride used in this embodiment is anhydrous hydrogen fluoride.

In this embodiment, too, the molar ratio of p-peroxytoluic acid to p-tolualdehyde is at least 1.0, preferably 1.0 to 1,5, especially preferably 1.0 to 1.3.

The reaction in accordance with this embodiment can be carried out either batchwise or continuously. When this embodiment is carried out batchwise, no particular restriction is imposed on the sequence of feeding the materials. However, the addition of hydrogen fluoride or a mixture of it with acetone to a mixture of p-tolualdehyde and p-peroxytoluic acid or a mixture of p-tolualdehyde and p-peroxytoluic acid with acetone induces an abrupt reaction and is very dangerous. Preferably, therefore, the materials are added in other sequences. For example, good results can be obtained by adding p-peroxytoluic acid to a mixture of p-tolualdehyde, hydroen fluoride and acetone (if used), or a mixture of p-peroxytoluic cid, hydrogen fluoride and acetone (if used) to p-tolualdehyde.

Since the hydrogen fluoride forms an azeotropic mixture with acetone in this embodiment, hydrogen fluoride is recovered together with acetone from the reaction mixture by distillation. The formation of an azeotrope between hydrogen fluoride and acetone in this embodiment is a new discovery of the inventors of the present application. According to the investigations of the inventors, the azeotropic mixture of hydrogen fluoride and acetone is a highest boiling azeotropic mixture having a boiling point of 91° C . at atmospheric pressure, and is composed of 52 mole % of hydrogen fluoride and 48 mole % of acetone. The mixture of hydrogen fluoride and acetone recovered can be re-used without any trouble. When the amount of the hydrogen fluoride in the reaction mixture is less than 0.5 in terms of its olar ratio to the total moles of the oxygen-containing compounds, the reaction can be carried out while distilling off only acetone at atmospheric or reduced pressure to increase the molar ratio of the hydrogen fluoride without distilling off the hydrogen fluoride. For example, when p-peroxytoluic acid is used as an acetone solution and the amount of acetone becomes excessive to decrease the above molar ratio to less than 0.5, the reaction is carried out while distilling ff the acetone from the reaction mixture to increase the molar ratio to 0.5 or more. When the above molar ratio is at least 0.5 but the molar ratio of hydrogen fluoride to acetone is less than 52/48, the reaction can be performed while distilling off acetone.

One of the advantages which arise from the use of p-peroxytoluic acid as an oxidizing agent in this embodiment is that there are less kinds of products than in the case of using other organic peroxy acids, and the separation of the products is easy. Since the organic acid necessarily formed after the oxidation of p-tolualdehyde with p-peroxytoluic acid is p-toluic acid which is also formed in a small amount from p-tolualdehyde by a side reaction, the number of the products is one less than in the case of using other organic peroxy acids. Another advantage is that the problem of recovering hydrogen fluoride as in the case of using hydrogen peroxide as an oxidizing agent can be obviated because p-peroxytoluic acid is obtained in a substantially anhydrous form by, for example, the autoxidation of p-tolualdehyde, and water is substantially not formed from the p-peroxytoluic acid. Still another advantage is that since p-peroxytoluic acid can be generally prepared by the autoxidation of p-tolualdehyde in this case, the number of raw materials can be one less than in the case of using other organic peroxy acids, and that even the partial autoxidation product mixture of p-tolualdehyde can be used as a solution containing p-tolualdehyde and p-peroxytoluic acid. Futhermore, p-toluic acid formed together with a formate ester of p-cresol can be converted to terephthalic acid by, for example, oxidation, and can therefore be a useful industrial material.

In this embodiment, p-tolualdehyde is oxidized to a formate ester of p-cresol smoothly and selectively by the superior catalytic action of hydrogen fluoride, and therefore, high purity p-cresol formate ester, and hence high purity p-cresol, can be obtained in high yields from high purity p-tolualdehyde.

One of the advantages arising from the use of acetone as a solvent in this embodiment is that acetone as a very good solvent for the synthesis of p-peroxytoluic acid can als be directly used as the solvent for preparation of the formate ester, and the industrial operation can be simplified. Another advantage is that since hydrogen fluoride and acetone form a highest boiling azeotropic mixture having an adequate boiling point, the evaporative scattering of hydrogen fluoride can be prevented by the presence of acetone in the reaction mixture in an amount exceeding that required to form the azeotrope, and that acetone and then a mixture of hydrogen fluoride and acetone can be readily separated and recovered by distillation. The acetone recovered can, as required, be recycled to the synthesis of p-peroxytoluic acid by the autoxidation of p-tolualdehyde. Since the hydrogen fluoride in the recovered mixture of hydrogen fluoride and acetone has sufficient activity, it can be recycled to the reaction of p-tolualdehyde with p-peroxytoluic acid. The concentration of hydrogen fluoride in the mixture of hydrogen fluoride with acetone can be increased up to 52 mole%. Since acetone is a ketone, it is theoretically possible that it undergoes oxidation with p-peroxytoluic acid by the Baeyer-Villiger reaction or it is condensed in the presence of an acid catalyst. However, under the conditions employed in this embodiment, it does not undergo any substantial change.

In this embodiment, a formate ester of p-cresol is prepared from p-tolualdehyde smoothly and selectively. p-Cresol, an industrially very important material, is prepared from the formate ester of p-cresol, and the hydrogen fluoride catalyst and the acetone solvent can be recycled as required. Morever, the starting p-tolualdehyde can be obtained with industrial advantage. Also, the p-pertoluic acid can be advantageously synthesized from p-tolualdehyde, and p-toluic acid formed at the same time is an industrially useful substance. For the above reason, this embodiment has a great industrial significance.

The above description has been directed to the embodiment of preparing a formate ester of p-cresol by oxidizing p-tolualdehyde with p-pertoluic acid. A formate ester of either o-cresol or m-cresol can be prepared under the same conditions using o-tolualdehyde or m-tolualdehyde instead of the p-tolualdehyde. The use of an isomeric mixture of tolualdehyde can affored an isomeric mixture of formate esters of cresols having the same proportions of the isomers as in the starting isomeric mixture. Furthermore, a formate ester of cresol can be prepared by oxidizing tolualdehyde with o-peroxytoluic acid or m-peroxytoluic acid instead of the p-peroxytoluic acid. There is no particular restriction on the combination of tolualdehydes and peroxytoluic acids. From the standpoint of the ease of separating the products, a combination of o-tolualdehyde and o-peroxytoluic acid, a combination of m-tolualdehyde and m-peroxytoluic acid, and a combination of p-tolualdehyde and p-peroxytoluic acid are preferred.

Preferably, the oxidation of tolualdehyde is carried out while distilling off acetone, and after the end of the oxidation of tolualdehyde, hydrogen fluoride and acetone are recovered.

The accompanying drawing is a flow chart for illustrating a preferred embodiment of performing the process of this invention continuously.

Referring to the drawing, p-tolualdehyde, air and acetone are introduced into an autoxidation apparatus 4 through paths 1, 2, and 3 respectively. Within the autoxidation apparatus 4, 40 1 to 60% of p-tolualdehyde is autoxidized to p-peroxytoluic cid. The exces of air is discharged through path 5. The autoxidation reaction mixture containing p-tolualdehyde and p-peroxytoluic acid is discharged through path 6. If desired, the molar ratio of p-peroxytoluic acid to p-tolualdehyde in this reac tion mixture is adjusted by the p-tolualdehyde coming out through path 7, and then, the reaction mixture is introduced into a reactor 9 through path 8. On the other hand, a mixture of hydrogen fluoride and acetone is introduced into the reactor 9 through path 10. The pressure inside the reactor 9 is maintained at a pressure which enables acetone to be distilled off at the reaction temperature. An acetone-distilling section of the reactor 9 is equipped with a rectifying column for distilling out only the acetone. By distilling off the acetone, the molar ratio of hydrogen fluoride in the reaction mixture to all the oxygen-containing compounds is maintained at 0.5 or more. In order to distill off only the acetone substantially, the molar ratio of acetone to hydrogen fluoride is maintained at 48/52 or more. The acetone which has been distilled off is recycled to the autoxidetion apparatus 4 through path 3 and re-used. In the reactor 9, p-tolualdehyde is oxidized with p-peroxytoluic acid to a formate ester of p-cresol. The reaction mixture in the reactor 9 is introduced into an aging tank 12 through path 11. In the aging tank 12, the oxidation of p-tolualdehyde is completed. The reaction product is introduced into a recovery tower 14 through path 13. A mixture of hydrogen fluoride and acetone recovered as the overhead product is recycled to the reactor 9 through path 10 and re-used. The bottoms containing a formate ester of p-cresol and p-peroxytoluic acid is introduced into a hydrolyzing tank 16 through path 15. In the hydrolyzation tank 16, the formate ester of p-cresol is hydrolyzed with water introduced through path 17 and is quantitatively converted to p-cresol. The hydrolyzed product is discharged through path 18, and p-cresol, p-touic acid and formic acid contained in it are isolated through a separating step The following Examples specifically illustrate the present invention.

EXAMPLE 1

A 200 cc. autoclave equipped with a stirrer was charged with 10.0 g of p-tolualdehyde and 12.0 g of glacial acetic acid, and with vigorous stirring, 8.6 g of anhydrous hydrogen fluoride was added. A solution prepared from 15.5 g of p-peroxytoluic acid crystals having a purity of 81.7% by weight and containing 18.3% by weig t of p-toluic acid as an impurity, 51.9 g of glacial acetic cid and 19.6 g of anhydrous hydrogen fluoride was added dropwise over the course of 10 minutes while maintaining the reaction temperature at −10° C. to +10° C. The stirring was continued for an additional 20 minutes at b 0° C., and then the reaction was stopped. The resulting reaction mixture was transferred into a plastic flask, and after attaching a fractional distillation column to the flask, it was heated over an oil bath. The hydrogen fluoride was distilled out and recovered in nearly all its amount. Methanol was added to the distillation residue, and the mixture was subjected to ester-interchange under reflux to convert the formate ester of p-cresol completely to p-cresol. As a result of gas-chromatographic analysis, the conversin of p-tolualdehyde was found to be 70.3%, and the yield of the formate ester of p-cresol based on the converted p-tolualdehyde was 77.7%.

EXAMPLE 2

The same autoclave as used in Example 1 was charged with 10.0 g of p-tolualdehyde, 18.0 g of anhydrous hydrogen fluoride and 27.0 g of glacial acetic acid, and with vigorous stirring, a solution prepared from 15.5 g of the ame p-peroxytoluic acid crystals as used in Example 1 and 27.0 g of glacial acetic acid was added dropwise over the course of 10 minutes while maintaining the reaction temperature at −10° C. to +20° C. The stirring was continued for an additional 20 minutes at 5° C and then the reaction was stopped. The resulting reaction mixture was treated and analyzed in the ame way as in Example 1. The conversion of p-tolualdehyde was found to be 100%, and the yield of the formate ester of p-cresol based on p-tolualdehyde was 88.1%.

EXAMPLE 3

The procedure of Example 2 was repeated except that 79.3 g of ethyl acetate was used instead of 54.0 g of glacial acetic acid. The conversion of p-tolualdehyde was found to be 93.6%, and the yield of the formate ester of p-cresol based on the converted p-tolualdehyde was 86.0%.

EXAMPLE 4

The same autoclave as used in Example 1 was charged with 10.1 g of 2,4-dimethylbenzaldehyde, 33.1 g of glacial acetic cid and 21.5 g of anhydrous hydrogen fluoride, and with vigorous stirring, a solution prepared from 14.1 g of p-peroxytoluic acid crystals and 20.7 g of glacial acetic acid as added dropwise over the course of 10 minutes while maintaining te reaction temperature at −10° C. to +10° C. The stirring was continued for an additional 20 minutes at 0° C., and then the reaction was stopped. The resulting reaction mixture was treated and analyzed in the same way as in Example 1. The conversion of 2,4-dimethylbenzaldehyde was found to be 100%, and the yield of a formate ester of 2,4-dimethylbenzaldehyde was 76.7%.

EXAMPLE 5

The ame autoclave as used in Example 1 was charged with 10.1 g of 2,4,5-trimethylbenzaldehyde, 49.9 g of glacial acetic acid and 20.0 g of anhydrous hydrogen fluoride, and with vigorous stirring, 13.6 g of the same p-peroxytoluic acid crystals as used in Example 1 were added portionwise over the course of 15 minutes while maintaining the reaction temperature at 0° t 10° C. The stirring was continued for an additional 20 minutes at 5° C., and then, the reaction was stopped. The resulting reaction mixture was treated and analyzed in the same way as in Example 1. The conversion of 2,4,5-trimethylbenzaldehyde was found to be 91.2%, and the yield of a formate ester of ,4,5-trimethylphenol based on the converted 2,4,5-trimethylbenzaldehyde was 84.6%.

EXAMPLE 6

The procedure of Example 5 was repeated except that the same amount of 4-isopropylbenzaldehyde was used instead of the 2,4,5-trimethylbenzaldehyde. The conversion of 4-isopropylbenzaldehyde was found to be 95.6%, and the yield of a formate ester of 4-isopropylphenol based on the converted 4-isopropylbenzaldehyde as 80.2%.

EXAMPLE 7

The ame procedure as in Example 2 was repeated except that 13.3 g of peroxybenzoic acid crystals having a purity of 90.2% and containing 9.8% of benzoic acid as an impurity were used instead of the p-peroxytoluic acid crystals. The conversion of p-tolualdehyde was found to be 100%, and the yield of a formate ester of p-cresol based on the p-tolualdehyde was 82.9%.

EXAMPLE 8

The same autoclave as used in Example 1 was charged with 10.0 g of p-tolualdehyde, 18.0 g of anhydrous hydrogen fluoride and 65.5 g of ethyl acetate, and with vigorous stirring, 22.9 g of an ethyl acetate solution containing 6.4 g of peroxyacetic acid was added dropwise and the same procedure as in Example 2 was performed. The resulting reaction mixture was treated and analyzed in the same way as in Example 1. The conversion of p-tolualdehyde was found to be 76.2%, and the yield of a formate ester of p-cresol based on the converted p-tolualdehyde was 72.7%.

EXAMPLE 9

An autoclave equipped with a stirrer was charged with 9.9 parts by weight of p-tolualdehyde and 25.5 parts by weight of acetone, and with vigorous stirring, 17.0 parts by weight of anhydrous hydrogen fluoride was added. A solution consisting of 12.7 parts by weight of p-peroxytoluic acid and 24.4 parts by weight of acetone was added dropwise over the course of 10 minutes while maintaining the temperature of the inside of the autoclave at −10° to +10° C. The stirring was continued for an additional 20 minutes at 0° C., and then the reaction was stopped. THe resulting reaction mixture was transferred to a corrosion-resistant plastic flask, and after attaching a distillation tower to the flask, it was heated over an oil bath to distill and recover the hydrogen fluoride and acetone in nearly all its amount. Methanol was added to the distillation residue, and the mixture was subjected to ester-interchange under reflux to convert the formate ester of p-cresol completely to p-cresol. As a result of gas-chromatographic analysis, the conversion of p-tolualdehyde was found to be 80.2%, and the selectivity of the formate ester of p-cresol from p-tolualdehyde was 83.5%.

EXAMPLE 10

The same autoclave as used in Example 9 was charged with 10.0 parts by weight of a tolualdehyde isomeric mixture comprising 96 mole% of p-tolualdehyde and 4 mole% of o-tolualdehyde, and with vigorous stirring, 14.0 parts by weight of anhydrous hydrogen fluoride was added dropwise while maintaining the temperature of the inside of the autoclave at −5° to +5° C. A solution prepared from 12.7 parts by weight of p-peroxytoluic acid and 26.0 parts by weight of acetone was added over the course of 15 minutes while maintaining the temperature of the inside of the autoclave at −5° to +5° C. The stirring was continued for an additional 20 minutes at 0° C., and then the reaction was stopped. The resulting reaction mixture was treated and analyzed in the same way as in Example 9. The conversion of the tolualdehyde isomeric mixture was found to be 95.4%, and the selectivities of a formate ester of p-cresol from p-tolualdehyde and of a formate ester of o-cresol from o-tolualdehyde were both 83.0%.

EXAMPLE 11

The same autoclave as used in Example 9 as charged with 10.0 parts by weight of p-tolualdehyde, and with vigorous stirring, a solution prepared from 12.7 parts by weight of p-peroxytoluic acid, 28.4 parts by weight of acetone and 15.0 parts by weight of anhydrous hydrogen fluoride was added dropwise over the course of 15 minutes while maintaining the temperature of the inside of the autoclave at −15° to 0° C. The stirring was continued for an additional 15 minutes at −7.5° C., and then the reaction was stopped. The resulting reaction mixture was treated and analyzed in the same way as in Example 9. The conversion of p-tolualdehyde was found to be 88.8%, and the selectivity of a formate ester of p-cresol from p-tolualdehyde was 92.1%.

EXAMPLE 12

The same autoclave as used in Example 9 was charged with a solution prepared from 12.8 parts by weight of p-peroxytoluic acid and 29.5 parts by weight of acetone, and with vigorous stirring, 25.2 parts by weight of anhydrous hydrogen fluoride was added dropwise while maintaining the temperature of the inside of the autoclave at −15° to "5° C. Then, 10.1 parts by weight of p-tolualdehyde was added dropwise over the course of 10 minutes while maintaining the temperature of the inside of the autoclave at −15° to −5° C. The stirring was continued for an additional 20 minutes a −10° C., and then, the reaction was stopped. The resulting reaction mixture was treated and analyzed in the same way as in Example 9. The conversion of p-tolualdehyde was found to be 86.4%, and the selectivity of a formate ester of p-cresol from p-tolualdehyde was 83.5%.

EXAMPLE 13

The same autoclave as used in Example 9 was charged with 23.0 parts by weight of acetone, and with vigorous stirring, 8.0 parts by weight of anhydrous hydrogen fluoride was added dropwise while maintaining the temperature of the inside of the autoclave at −15° to −5° C. to prepare a solution in which the molar ratio of hydrogen fluoride to acetone was 1. A solution prepared from 6.1 parts by weight of p-peroxytoluic acid, 25.0 parts by weight of acetone and 4.8 parts by weight of p-tolualdehyde was added dropwise within 1 minute while maintaining the temperature of the inside of the autoclave at −15° to −5° C. Then, a rectifying colum was attached to the autoclave, and the temperature of the inside of the autoclave was gradually raised to 20° C. over the course of about 2 hours at a pressure of about 30 mmHg, and the reaction was performed while distilling off only acetone. The amount of acetone recovered by distillation was 26.6 parts by weight. The resulting reaction mixture was analyzed by iodometric titration, and the conversion of p-peroxytoluic acid was found to be 92.0%. The reaction mixture was transferred to a corrosion-resistant plastic flask, and after attaching a distillation column to the flask, it was heated over an oil bath to distill and recover hydrogen fluoride and the remaining acetone. The mixture of hydrogen fluoride and acetone recovered consisted of 8.0 parts by weight of hydrogen fluorie and 21.4 parts by weight of acetone. Methanol was added to the distillation residue remaining in the flask and the mixture was subjected to esterinterchange to convert a formate ester of p-cresol completely to p-cresol. As a result of gas-chromatographic analysis; the conversion of p-tolualdehyde was found to be 97.8 %. The selectivity of the formate ester of p-cresol from p-tolualdehyde was 79.3%.

EXAMPLE 14 p-Cresol was continuously prepared from p-tolualdehyde in accordance with the flow chart shown in the drawing. The details were as follows:

An autoxidation apparatus 4 was charged with 330 parts by weight/hour of p-tolualdehyde through path 1, 927 parts by weight/hour of air through path 2, and 660 parts by weight/hour of acetone through path 3. In the autoxidation apparatus 4, the pressure was adjusted to 20 atmospheres, the temperature to 40° C., and the residence time to 0.6 hour. The excess of air was discharged through path 5. The resulting autoxidation reaction mixture containing 136 parts by weight/hour of p-tolualdehyde, 172 parts by weight/hour of p-peroxytoluic acid, 66 parts by weight/hour of by-product p-toluic acid and 660 parts by weight/hour of acetone was discharged through path 6, and via path 8, introduced into a reactor 9. At this time, it was unnecessary to adjust the molar ratio of the p-peroxytoluic acid to the p-tolualdehyde by p-tolualdehyde through path 7. On the other hand, 880 parts by weight/hour of an equimolar mixture of hydrogen fluoride and acetone was introduced into the reactor 9 through path 10. In the reactor 9, the pressure was adjusted to 30 mmHg, the temperature to 10° C., and the residence time to 0.25 hour. A rectifying column having 10 theoretical trays which was provided in the acetone distilling section of the reactor 9 was operated at a reflux ratio of 1, and 660 parts by weight/hour of acetone was discharged through path 3, and recycled to the autoxidation apparatus 4. The reaction mixture in the reactor 9 was introduced into an aging tank 12 through path 11 at a rate of 1254 parts by weight/hour. In the aging tank 12, the pressure was atmospheric pressure, the temperature was 10° C., and the residence time was 0.25 hour. 1,254 Parts by weight/hour of the reaction mixture in the aging tank 12 was introduced into a recovery tower 14 through path 13. In the recovery tower 14 having three theoretical trays, the pressure was atmospheric pressure, the temperature of the top of the tower was 90° C., and the reflux ratio was maintained at 1. From the top of the recovery tower 14,880 parts by weight/hour of an equimolar mixture of hydrogen fluoride and acetone was discharged, and recycled to the reactor 9 through path 10. From the bottom of the recovery tower 14, 374 parts by weight/hour of the bottoms product was discharged, and introduced into a hydrolyzation tank 16 through path 15. On the other hand, 170 parts by weight/hour of water was introduced into the hydrolyzation tank 16 through path 17. In the hydrolzation tank 16, the pressure was atmospheric pressure, the temperature was 100° C., and the residence time was 1 hour. The hydrolyzed reaction mixture containing 100 parts by weight/hour of p-cresol, 247 parts by weight/hour of p-toluic acid, 43 parts by weight/hour of formic acid, 1 parts by weight/hour of p-tolualdehyde, and water was discharged through path 18.

What we claim is:

1. A process for preparing formate esters of the formula

HCOOAr 

wherein Ar is an aromatic hydrocarbon group containing alkyl aromatic aldehyde of the general formula ArCHO 

wherein Ar is the same as defined above, with an organic peroxy acid in the presence of hydrogen fluoride in the presence or absence of a solvent under the conditions that (1) the molar ratio of the organic peroxy acid to the alkyl aromatic aldehyde is 1.0 to 1.5 : 1 and (2) the molar ratio of the hydrogen fluoride to all the oxygen-containing compounds is 0.5 to 4.0: 1.

2. The process of claim 1 wherein the lower alkyl groups each contain 1 to 3 carbon atoms.

3. The process of claim 1 wherein the organic peroxy acid is p-peroxytoluic acid, peroxybenzoic acid or peroxyactic acid.

4. The process of claim 1 wherein the solvent is a lower aliphatic carboxylic acid, ester, ether or ketone.

5. The process of claim 1 wherein the oxidation reaction is carried out in a substantially anhydrous condition, and after the end of the oxidation the hydrogen fluoride is recovered singly or together with the solvent.

6. The process of claim 1 wherein the molar ratio of the hydrogen fluoride to the alkyl aromatic aldehyde is 3 to 20:1.

7. The process of claim 6 wherein a lower aliphat ic carboxylic acid, ester, ether or ketone is used in an amount such that the molar ratio of hydrogen fluoride to all the amount of oxygen-containing compounds becomes 0.5 to 4.0:1.

8. The process of claim 1 wherein the oxidation reaction temperature is −50° to +50° C.

9. The process of claim 1 wherein the oxidation reaction is carried out in the liquid phase.

10. The process of claim 1 wherein the organic peroxy acid is p-peroxytoluic acid obtained by autoxidation of p-tolualdehyde.

11. The process of claim 1 wherein Ar in the two formulae is an o-, m- or p-tolyl group, the organic peroxy acid is o-, m- or p-peroxytoluic acid, the solvent is acetone, and the oxidation reaction is carried out in a substantially anhydrous condition.

12. The process of claim 1 wherein Ar in the two formulae is an o-, m- or p-tolyl group, the organic peroxy acid is o-, m- or p-peroxytoluic acid, the solvent is acetone, and the oxidation is carried out in a substantially anhydrous condition while distilling off the acetone, and after the end of the oxidation reaction, a mixture of the hydrogen fluoride and acetone is recovered.

13. The process of claim 1 wherein Ar in the two formulae is a p-tolyl group, the organic peroxy acid is p-peroxytoluic acid obtained by autoxidation of p-tolualdehyde in acetone, the solvent is acetone, the molar ratio of the organic peroxy acid to the alkyl aromatic aldehyde is 1.0 to 1.3:1, and the oxidation reaction is carried out in a substantially anhydrous condition.

* * * * *